United States Patent [19]

Young et al.

[11] Patent Number: 4,500,337

[45] Date of Patent: * Feb. 19, 1985

[54] ADHERENT CONTROLLED RELEASE MICROBIOCIDES CONTAINING HYDROLYZABLE SILANES AND ORGANIC TITANIUM COMPOUNDS

[76] Inventors: Robert W. Young, 101 W. 55th St., New York, N.Y. 10019; Samuel Prussin, Partington Ridge, Big Sur, Calif. 93920; Norman G. Gaylord, 28 Newcomb Dr., New Providence, N.J. 07974

[*] Notice: The portion of the term of this patent subsequent to Apr. 15, 1997 has been disclaimed.

[21] Appl. No.: 183,765

[22] Filed: Sep. 3, 1980

[51] Int. Cl.³ ............................................. A01N 25/00
[52] U.S. Cl. .................... 71/67; 71/DIG. 1; 71/64.11; 106/15.05; 424/78; 427/2; 427/4
[58] Field of Search .................. 71/67, 64 F, DIG. 1; 424/78; 427/2, 4

[56] References Cited

U.S. PATENT DOCUMENTS 4,198,441  4/1980  Young et al. ........................ 427/2
4,200,664  4/1980  Young et al. ........................ 427/4

*Primary Examiner*—Catherine L. Mills
*Attorney, Agent, or Firm*—Roylance, Abrams, Berdo & Goodman

[57] ABSTRACT

There are disclosed methods and compositions for the controlled release of microbiocides by using a mixture consisting of (a) a hydrolyzable silane or an organopolysiloxane containing hydrolyzable silane groups or a partial hydrolyzate thereof, (b) a hydrolyzable organic titanium compound or a partial hydrolyzate thereof, (c) optionally, an organopolysiloxane containing hydroxyl groups or a carbinol-containing polymer, and (d) a microbiocide.

36 Claims, No Drawings

ADHERENT CONTROLLED RELEASE MICROBIOCIDES CONTAINING HYDROLYZABLE SILANES AND ORGANIC TITANIUM COMPOUNDS

FIELD OF THE INVENTION

The present invention relates to methods and compositions for the controlled release of microbiocides. The present invention is concerned with stable compositions which, after application to a suitable substrate and exposure to the atmosphere, undergo in situ chemical reaction resulting in adhesion to the substrate and the controlled releaase of biocides for the control of microorganisms, particularly those possessing procaryotic cells, such as bacteria and bluegreen algae, and viruses in which the unit of structure is the virion rather than the cell.

BACKGROUND OF THE INVENTION

The utilization of microbiocides for the control and destruction of microorganisms has long been a matter of great importance and has taken on even more importance as a result of the growing awareness of the expense and problems caused by the uncontrolled growth of microorganisms. Such microbiocides are generally referred to as antimicrobials, antiseptics, disinfectants, sanitizers, germicides, bactericides, antiviral agents, algaecides, slimicides, antifouling agents and preservatives.

Microbiocides are used in surface disinfection in private homes as well as in commercial, institutional and public buildings, in communal toilet facilities and swimming pool and changing rooms, in food processing plants and food service facilities and in industrial and building recirculating cooling water systems. They are used to treat many types of surfaces such as walls, floors, paintwork, lavatories, sinks and bench tops. Microbiocides are also applied to marine construction including buildings, off-shore drilling rigs and marine vessels as components of antifouling marine coatings. Microbiocides are also applied to human and animal skin and other surfaces.

The microbiocides are generally effective only as long as they persist on the substrate to which they are applied. Consequently, frequent application is necessary.

The principles of antimicrobial activity have been enunciated by J. F. Gardiner ("Disinfection, Sterilization, and Preservation", edited by S. S. Block, 2nd Edition, Lea & Febiger, Philadelphia, Pa., 1977, Chapter 43, p. 883). Antimicrobial activity occurs when a physical or chemical agent interacts with a component of the organism which is essential to its structure or metabolism. The target may be a cell constituent or a single enzyme.

Effective contact between the microbiocide and the microorganism is an essential prerequisite for antimicrobial action. It is influenced by physical barriers and by soluble or particulate substances in the environment which inactivate or reduce the concentration of the microbiocide by adsorption. Adsorption or uptake of the latter by microorganisms depends on the bonds which are formed between the molecules of the microbiocide and the cell surface, e.g. van der Waals bonds, hydrogen bonds, ionic bonds and covalent bonds. Notwithstanding the nature of the ultimate bonding, effective contact is necessary before the penetration of chemicals to the cell membrane or cytoplasm can occur.

Microorganisms are the smallest living creatures, with the shortest generation times and the greatest population densities. They possess a unique ability to survive in different and oftentimes hostile environments and to reinvade, grow, reproduce and reinfect an area which has only newly been freed of contamination. Since the growth rate of microbial populations is generally exponential, a reduction in a given population is not adequate. Total sterilization, disinfection and/or sanitation is necessary, since an environment cannot be "practically sterile". Consequently, antimicrobial treatment must be immediately effective and frequent.

Pesticides, particularly insecticides, are utilized in the elimination of more complex organisms with longer life cycles and, generally, various stages of development, each of which may be susceptible to pesticidal action. The frequency of application of a pesticide to prevent reinfestation is many orders of magnitude less than that necessary in the case of a microbiocide. Further, pest elimination may only be necessary during certain seasons, e.g. during the period when the destructive stage of the insect's life cycle is generated or during the growth stage of a plant.

The modern development of controlled release pesticides, particularly insecticides, has resulted in extension of the duration between applications and thus increased the efficiency and economy of control in agricultural and non-agricultural applications.

The controlled release of insecticides has been achieved by their incorporation within a polymeric matrix, e.g. encapsulation wherein a pesticide is surrounded by an enveloping polymeric wall that permits escape through diffusion, permeation or degradation; dispersion of the pesticide in an elastomer or a plastic wherein the pesticide is released through leaching or diffusion; and the chemical combination of the pesticide with a polymer in such a manner that the appended pesticide slowly breaks off the polymeric backbone upon exposure to the pest infested environment, e.g by hydrolysis of the linkage.

In view of the need to obtain intimate, and in most cases, immediate, contact between a microorganism and a sufficient concentration of a microbiocide to have a lethal effect, the encapsulation, dispersion or chemical bonding of the latter within a polymeric matrix would not be expected to control the release of the toxic agent, while also providing for the speed and efficiency of action required to eliminate microorganism contamination. Consequently, the methods generally used for the controlled release of pesticides, including insecticides, fungicides and herbicides, would not be applicable to the effective controlled release of microbiocides. Further, the various approaches indicated above for the controlled release of pesticides failed to provide for adequate adhesion of the pesticide within the polymeric matrix to the substrate. This permitted the removal or transfer of the material from the substrate as a result of physical contact or atmospheric conditions.

The simultaneous development of adhesion to the substrate and controlled release characteristics, has recently been achieved by the discovery of compositions containing pesticides and moisture-reactive components which, on exposure to the atmosphere, undergo adhesion-promoting crosslinking reactions to form polymer networks which control pesticide release, while remaining strongly adherent to the substrate.

Surprisingly, it has now been found that the adherent, crosslinking sites which are generated due to the presence of the moisture-reactive components are capable of permitting the release of a microbiocide rapidly enough for effective elimination of a microorganism, while controlling and prolonging the duration of the release.

SUMMARY OF THE INVENTION

An object of the present invention is to provide a process for the controlled release of microbiocides, removing the above-described defects of the prior art processes. Another object of the present invention is to provide compositions capable of undergoing in situ chemical reaction after application to a substrate and exposure to the atmosphere, resulting in adhesion of the microbiocide and increased effective lifetime.

It has now been found that these improvements in controlled release microbiocides are achieved by using a mixture consisting of (a) a hydrolyzable silane or an organopolysiloxane containing hydrolyzable silane groups or partial hydrolyzates thereof, (b) a hydrolyzable organic titanium compound or a partial hydrolyzate thereof, (c) optionally a hydroxyl-containing polymer selected from the group consisting of (1) an organopolysiloxane containing hydroxyl groups or functional groups which are hydrolyzable to hydroxyl groups, and (2) a carbinol-containing polymer, and (d) a microbiocide.

Thus, the present invention provides compositions capable of undergoing adhesion-promoting, crosslinking reactions, to form polymeric networks with controlled release characteristics.

DETAILED DESCRIPTION OF THE INVENTION

In U.S. Pat. No. 4,200,664, it was disclosed that a mixture consisting of a hydrolyzable silane or an organopolysiloxane containing hydrolyzable silane groups or partial hydrolyzates thereof, a hydrolyzable organic titanium compound or a partial hydrolyzate thereof, and an insecticide, is capable of undergoing crosslinking reactions to form adherent polymeric networks for the controlled release of the insecticide incorporated therein. In U.S. Pat. No. 4,198,441, it was disclosed that the mixture consisting of a hydrolyzable silane or an organopolysiloxane containing hydrolyzable silane groups, a hydrolyzable organic titanium compound and an insecticide, may also contain an organopolysiloxane containing hydroxyl groups or functional groups which are hydrolyzable to hydroxyl groups. In our co-pending application Ser. No. 092,632, filed Nov. 8, 1979, it was disclosed that the mixture consisting of a hydrolyzable silane or an organopolysiloxane containing hydrolyzable silane groups, a hydrolyzable organic titanium compound and an insecticide, may also contain a carbinol-containing organic polymer.

It has now been found that the mixture of hydrolyzable silane or organopolysiloxane containing hydrolyzable silane groups and hydrolyzable organic titanium compound, per se as disclosed in U.S. Pat. No. 4,200,664, or in admixture with either an organopolysiloxane containing hydroxyl groups or functional groups which are hydrolyzable to hydroxyl groups, as disclosed in U.S. Pat. No. 4,198,441, or a carbinol-containing organic polymer, as disclosed in our co-pending application Ser. No. 092,632, may also be used with the microbiocides of the present invention.

The hydrolyzable silanes suitable for use in the practice of the present invention have the formula $$R_nSiX_{4-n}$$

where R is a monovalent hydrocarbon radical, X is a hydrolyzable group such as halogen, alkoxy, acyloxy, hydrogen and the like, and n is an integer from 0 to 2, inclusive. When X is an alkoxy group OR′ or an acyloxy group OCOR′, R′ may be methyl, ethyl, propyl, isopropyl, butyl, isobutyl, secondary butyl, 2-ethylhexyl or other aliphatic hydrocarbon radical of less than 10 carbon atoms. Preferably R′ is a lower alkyl radical of no more than 4 carbon atoms. All of the X's may be the same or they may be different. The hydrocarbon radical R may be cyclic or acyclic, saturated or unsaturated, aliphatic or aromatic and include the alkyl, aryl, alkenyl, aralkenyl, cycloalkyl, cycloalkenyl and heterocyclic radicals such as methyl, ethyl, propyl, isopropyl, butyl, isobutyl, secondary butyl, tertiary butyl, amyl, hexyl, vinyl, allyl, chloroallyl, methallyl, crotyl, butadienyl, phenyl, dichlorophenyl, pentachlorophenyl, xylyl, benzyl, styryl, cinnamyl, furfuryl, cyclohexyl, cyclopentadienyl, cyclopentenyl, pyridyl, etc. radicals. The hydrocarbon radical R may also be a substituted alkyl $R''(CH_2)_x$ where x is an integer from 1 to 20 inclusive and R″ is a polar and/or reactive functionality such as acryloxy, methacryloxy, glycidoxy, epoxycyclohexyl, mercapto, amino, ureido, halo, etc. radicals. There are numerous commercial materials of this type which are commonly known as organofunctional silane coupling agents or adhesion promoters.

The monomeric hydrolyzable silanes may be subjected to partial hydrolysis to promote the formation of condensation products which are still hydrolyzable silanes and are suitable for use in the practice of the present invention.

The organopolysiloxanes containing pendant or terminal hydrolyzable silane radicals, suitable for use in the practice of the present invention, have the formula $$P\text{-}(SiX_n)_m$$

where P is an organopolysiloxane as hereinafter defined, X is a hydrolyzable group such as halogen, alkoxy, acyloxy, hydrogen and the like, n is an integer from 2 to 3 and m is an integer from 1 to 20. When X is an alkoxy group OR′ or an acyloxy group OCOR′, R′ may be methyl, ethyl, propyl, isopropyl, butyl, isobutyl, secondary butyl, 2-ethylhexyl or other aliphatic hydrocarbon radical of less than 10 carbon atoms. Preferably R′ is a lower alkyl radical of no more than 4 carbon atoms. All the X's may be the same or they may be different.

The organopolysiloxanes are well known in the art and contain the structural unit 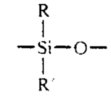 where R and R′ are oxygen or non-hydrolyzable hydrocarbon or substituted hydrocarbon radicals and are the same or different. When R and R′ are hydrocarbon radicals, they may be acyclic or cyclic, saturated or unsaturated and include aliphatic radicals such as methyl, ethyl, vinyl, propyl, allyl, butyl, crotyl, hexyl, decyl, dodecyl, hexadecyl, octadecyl, octadecenyl radicals and the like, as well as halogenated or other substituted aliphatic radicals, aromatic radicals such as phenyl, biphenyl, phenoxyphenyl and naphthyl as well as halogenated and other substituted aromatic radicals, aralkyl radicals such as benzyl and phenylethyl radicals, alkylaryl radicals such as tolyl and xylyl radicals, cycloaliphatic radicals such as cyclopropyl, cyclopentyl, cyclopentenyl, cyclohexyl and cyclohexenyl radicals and heterocyclic radicals such as furfuryl radicals.

The organopolysiloxanes may be linear, branched or both linear and branched. The polysiloxane may be predominantly a monoorganopolysiloxane, a diorganopolysiloxane, a copolymer containing monoorganosiloxane units and diorganosiloxane units, a copolymer containing triorganosiloxane units and $SiO_2$ units and the like. Notwithstanding the predominant structure, the organopolysiloxane may contain varying amounts of other structural units, in addition to hydrolyzable silane radicals.

The polysiloxanes containing hydrolyzable silane radicals, suitable for use in the practice of the present invention, may be prepared from organopolysiloxanes which are well known in the art. The latter may be prepared by various procedures including controlled hydrolysis of appropriate precursors as well as ring opening polymerization of cyclic organopolysiloxanes.

The controlled hydrolysis and cohydrolysis of $RSiX_3$, $R_2SiX_2$, $R_3SiX$ and $SiX_4$, where X is a hydrolyzable radical as previously defined, yields organopolysiloxanes containing monoorganosiloxane, diorganosiloxane, triorganosiloxane and $SiO_2$ units, respectively. The relative proportions of said units in the organopolysiloxane are determined by employing the appropriate proportions of hydrolyzable precursors. In order to be useful in the preparation of polysiloxanes containing hydrolyzable silane radicals, the precursor organopolysiloxanes must be readily soluble or dispersible in organic solvents and contain residual reactive radicals such as hydroxyl, alkoxyl, acyloxyl, halogen, hydrogen, vinyl, allyl and the like.

The polymerization of cyclic organopolysiloxanes provides another route to the preparation of organopolysiloxanes containing reactive radicals which may be employed in the preparation of the organopolysiloxanes containing hydrolyzable silane radicals which are suitable for use in the practice of the present invention. These and other methods of preparation are set forth in K. A. Andrianov, "Metalorganic Polymers", Interscience Publishers, New York, 1965, Chapter III, pages 109–275, the disclosures of which are incorporated herein by reference.

Polysiloxanes which are at an intermediate stage of polymerization in that they contain hydroxyl radicals which, upon application of heat, may undergo condensation to a more advanced stage of polymerization or in that they contain hydrolyzable groups which upon further hydrolysis may proceed to a more advanced stage of polymerization, if they have not been rendered insoluble in organic solvents, are suitable precursors for the preparation of the organopolysiloxanes containing hydrolyzable silanes which may be used in the practice of the present invention.

The organopolysiloxanes containing hydrolyzable silanes may be prepared by reactions well known in the art. Thus, reaction of an organopolysiloxane containing hydroxyl groups with excess silicon tetraacetate yields the triacetoxysilane.

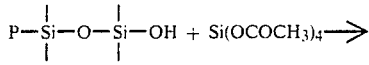

Similarly, reaction with an alkyl or aryltriacetoxysilane yields the corresponding diacetoxysilane, as disclosed in U.S. Pat. No. 3,035,016, the disclosures of which are incorporated herein by reference.

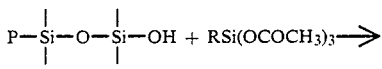

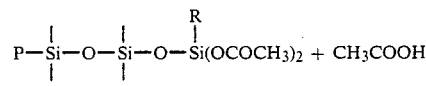

The reaction of an organopolysiloxane containing SiH units, e.g. as prepared by hydrolysis or cohydrolysis of a dichlorosilane with an unsaturated trialkoxysilane or triacyloxysilane in the presence of chloroplatinic acid, yields an organopolysiloxane containing hydrolyzable radicals, suitable for use in the practice of the present invention.

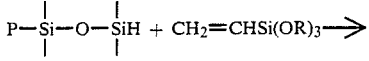

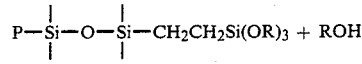

Organopolysiloxanes containing vinyl unsaturation, e.g. as prepared by cohydrolysis of mixtures of various chlorosilanes including vinylalkylchlorosilanes, may be reacted with trialkoxysilane to yield organopolysiloxanes containing hydrolyzable silane radicals suitable for use in the present invention.

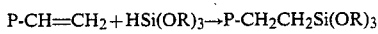

Alternative methods of preparing organopolysiloxanes suitable for use in the practice of the present invention, will be obvious to those skilled in the art. Notwithstanding the method of preparation, the presence of $SiX_{2-3}$ radicals as pendant or terminal units in an organopolysiloxane renders it suitable for use in the present invention.

The organopolysiloxanes containing hydrolyzable silane radicals may be fluids of low or high viscosity or even solids. The physical appearance of the polysiloxane is dependent upon the nature of the R and R' radicals, the presence of linear or branched structures as well as the molecular weight. Notwithstanding the physical appearance of the polysiloxane, the important requirement for utility in the practice of the present invention is the presence of hydrolyzable silane radicals. Mixtures of such polysiloxanes are suitable for use in the present invention.

While hydrolyzability is a general characteristic of the silanes which may be used in the practice of the present invention, the rate of hydrolysis is a function of the nature of the hydrocarbon substituent in the hydrolyzable group. Thus, the presence of methyl radicals results in rapid hydrolysis while higher alkyl radicals result in slower hydrolysis. In the latter case it is possible to use water as a diluent or dispersing medium during the preparation and handling of the active compositions, and as the hydrolyzing reactant as the composition is applied or after it is applied to the substrate.

The hydrolyzable titanium compounds which are suitable for use in the practice of the present invention are the tetraesters, tetraanhydrides and tetraamides of orthotitanic acid.

The titanium tetraesters have the formula

Ti(OR)$_4$ where R is an aliphatic hydrocarbon radical of less than about 20 carbon atoms and may be saturated or unsaturated and acyclic or cyclic. Thus, R may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. Titanium orthoesters where R is the same or mixed are suitable for use in the present invention. Partially hydrolyzed orthoesters may also be used if the hydrolysis has not rendered them insoluble in organic solvents and they still retain alkoxy groups.

The titanium tetraanhydrides have the formula

Ti(OCOR')$_4$ where R' is an aliphatic hydrocarbon radical of less than about 20 carbon atoms and may be saturated or unsaturated and acyclic or cyclic. Thus, R' may be methyl, ethyl, allyl, propyl, isopropyl, butyl, isobutyl, secondary butyl, tertiary butyl, 2-ethylhexyl, octyl, nonyl, decyl, undecyl, dodecyl, octadecyl and the like. The anhydrides or acylates may also be prepared from aliphatic acids which contain more than one carboxyl group, such as maleic acid, fumaric acid, etc. Titanium acylates where R' is the same or mixed are suitable for use in the present invention. Mixed alkoxytitanium acylates are also useful. These are prepared by the reaction of a tetraester with an acid or anhydride or of a tetraanhydride with an alcohol under anhydrous conditions. Partially hydrolyzed acylates may also be used.

The titanium tetraamides have the formula

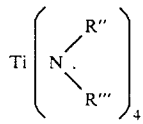

where R'' is hydrogen, alkyl or aryl and R''' is alkyl or aryl. The alkyl groups may be saturated or unsaturated and acyclic or cyclic and include methyl, ethyl, propyl, butyl, amyl, octyl, stearyl, oleyl, etc. groups.

The titanium polymers prepared by partial hydrolysis of the monomeric titanium orthoesters, acylates and amides, per se or in admixture, as well as by partial hydrolysis of mixed orthoesters, acylates and amides may be used in the practice of the present invention.

While hydrolyzability is a general characteristic of the tetraesters, tetraanhydrides and tetraamides of orthotitanic acid which may be used in the practice of the present invention, the rate of hydrolysis is a function of the nature of the hydrocarbon substituent. Thus, the presence of methyl, ethyl and other lower alkyl substituents results in rapid hydrolysis while higher alkyl substituents result in slower hydrolysis. In the latter case it is possible to use water as a diluent or dispersing medium during the preparation and handling of the active compositions, and as the hydrolyzing reactant as the composition is applied or after it is applied to the substrate.

An alternative approach to delayed hydrolysis is the use of an organic titanium chelate. The chelates which are suitable for use in the practice of the present invention are either water soluble or solvent soluble and hydrolyze slowly in aqueous systems per se or when the pH is changed or the temperature is raised.

The titanium chelates are derivatives of bi- or multifunctional compounds in which one of the functional groups is usually hydroxyl or enolic carbonyl and the other group is hydroxyl, carboxyl, carbonyl or amino. Thus, the titanium chelates are derivatives of glycols, hydroxy acids, dicarboxylic acids, diketones, ketoesters or alkanolamines. Representative chelates include chelates of 2-methylpentane-2,4-diol, 2-ethylhexane-1,3-diol, 2-methylpentane-1,3-diol, 2-propylheptane-1,3-diol, lactic acid, glycolic acid, citric acid, tartaric acid, hydroxystearic acid, oxalic acid, acetylacetone, ethyl acetoacetate, diethanolamine, triethanolamine and the like.

The titanium chelates are generally prepared by the reaction of a titanium alkoxide such as tetraisopropyl titanate and the appropriate bi- or multifunctional compound. The preparation and properties of the titanium chelates are disclosed in Kirk-Othmer Encyclopedia of Chemical Technology, John Wiley & Sons, New York. 2nd Edition, Volume 20, pages 464–468 (1969). The preparation of aqueous solutions of the titanium chelates is described in "Tyzor Organic Titanates", E. I. duPont de Nemours & Co., Organic Chemicals Department, Technical Bulletin D-5258. The disclosures of each of the hereinabove identified references are incorporated herein by reference.

The organopolysiloxanes suitable for use in the practice of the present invention are well known in the art and contain the structural unit

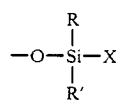

where X is a hydroxyl radical or a hydrolyzable radical such as alkoxy, acyloxy, hydrogen, halogen and the like and R and R' are oxygen or non-hydrolyzable hydrocarbon or substituted hydrocarbon radicals and are the same or different. When R is a hydrocarbon radical it may be acyclic or cyclic, saturated or unsaturated and includes aliphatic radicals such as methyl, ethyl, vinyl, propyl, allyl, butyl, crotyl, hexyl, decyl, dodecyl, hexadecyl, octadecyl, octadecenyl radicals and the like as well as halogenated or other substituted aliphatic radicals, aromatic radicals such as phenyl, biphenyl, phenoxyphenyl and naphthyl radicals as well as halogenated and other substituted aromatic radicals, aralkyl radicals such as benzyl and phenylethyl radicals, alkylaryl radicals such as tolyl and xylyl radicals, cycloaliphatic radicals such as cyclopropyl, cyclopentyl, cyclopentenyl, cyclohexyl and cyclohexenyl radicals and heterocyclic radicals such as furfuryl radicals.

Two organopolysiloxanes may be linear, branched or both linear and branched and the X radicals may be terminal end groups or may be situated at other sites in the polysiloxane chain. The number of X radicals may range from one radical per polysiloxane molecule up to 30 weight percent of the total organopolysiloxane molecular weight.

The polysiloxane may be predominantly a monoorganopolysiloxane, a diorganopolysiloxane, a copolymer containing monoorganosiloxane units and diorganosiloxane units, a copolymer containing triorganosiloxane units and $SiO_2$ units and the like. Notwithstanding the predominant structure, the organopolysiloxane may contain varying amounts of the other structural units in addition to hydroxyl radicals or radicals hydrolyzable thereto.

The polysiloxanes suitable for use in the practice of the present invention are well known in the art and may be prepared by various procedures including controlled hydrolysis of appropriate precursors as well as ring opening polymerization of cyclic organopolysiloxanes.

The controlled hydrolysis and cohydrolysis of $RSiX_3$, $R_2SiX_2$, $R_3SiX$ and $SiX_4$, where X is a hydrolyzable radical as previously defined, yields organopolysiloxanes containing monoorganosiloxane, diorganosiloxane, triorganosiloxane and $SiO_2$ units, respectively. The relative proportions of said units in the organopolysiloxane are determined by employing the appropriate ratios of hydrolyzable precursors. In order to be useful in the practice of the present invention, the resultant organopolysiloxane must be readily soluble or dispersible in organic solvents and contain residual hydroxyl or hydrolyzable radicals.

The polymerization of cyclic organopolysiloxanes provides another route to the preparation of organopolysiloxanes containing hydroxyl or hydrolyzable radicals which may be employed in the practice of the present invention. These and other methods of preparation are set forth in K. A. Andrianov, "Metalorganic Polymers", Interscience Publishers, New York, 1965, Chapter III, pages 109–275, the disclosures of which are incorporated herein by reference.

Polysiloxanes which are at an intermediate stage of polymerization in that they contain hydroxyl radicals which, upon application of heat, may undergo condensation to a more advanced stage of polymerization or in that they contain hydrolyzable groups which upon further hydrolysis may proceed to a more advanced stage of polymerization are suitable for use in the practice of the present invention if they have not been rendered insoluble in organic solvents.

The organopolysiloxanes may be fluids of low or high viscosity or even solids. The physical appearance of the polysiloxane is dependent upon the nature of the R and R' radicals, the presence of linear or branched structures as well as the molecular weight. Notwithstanding the physical appearance of the polysiloxane, the important requirement for utility in the practice of the present invention is the presence of hydroxyl radicals or radicals hydrolyzable thereto. Mixtures of such polysiloxanes are suitable for use in the present invention.

The carbinol-containing polymers which are suitable for use in the practice of the present invention, include synthetic polymers, natural polymers and chemically modified natural polymers.

Polyalkylene oxides prepared by reaction of alkylene oxides such as ethylene oxide, propylene oxide, styrene oxide, epichlorohydrin, etc., with compounds containing active hydrogen atoms are reactive components in the compositions of the present invention. The effective polyethers may be obtained by oxyalkylation of polyfunctional active hydrogen compounds containing hydroxyl, phenolic, carboxyl, amino, amido, mercapto and other groups. The functional groups may be terminal or pendant groups on linear or branched simple molecules or polymers and the latter may be random, alternating, block or graft copolymers.

Polyesters containing pendant or terminal hydroxyl groups are capable of undergoing crosslinking reactions with the hydrolyzable compounds of the present invention. Effective polyesters include saturated polyesters based on glycol-dicarboxylic acid or glycol-dicarboxylic acid anhydride condensation. Unsaturated polyesters based on maleic anhydride-glycol condensation and similar polyesters are also crosslinked by the hydrolyzable metal compounds. Alkyd resins, containing pendant unsaturation from tung oil, linseed oil, etc., and having branched structures from the incorporation of glycerol or pentaerythritol into the glycol-acid or -anhydride reaction mixture are also suitable crosslinkable polymers.

Polycaprolactone polyester polyols prepared by the reaction of caprolactone with polyol or similar initiators represent an inherently useful group of saturated polyesters with terminal hydroxyl groups, in that they are biodegradable and provide a route to a crosslinked polymer matrix which may be degraded after completing its function as a controlled release matrix.

Epoxy resins containing internal hydroxyl groups, hydrolyzed epoxy resins containing terminal and penultimate hydroxyl groups, reduced epoxy resins containing terminal or internal hydroxyl groups, hydrolyzed epoxy ester resins, etc., are crosslinkable polymers in the present invention. The epoxy resins may be based on bisphenols, glycols, polyols, novolac phenolic resins, epoxidized polybutadiene or other unsaturated diene or vinyl polymer or copolymer, epoxidized soybean oil, etc. The hydroxyl-containing epoxy resins and hydrolyzed epoxy or epoxidized resins undergo crosslinking with the hydrolyzable metal compounds of the present invention to provide adherent polymer matrices or networks.

Formaldehyde-condensation products with phenols, aromatic amines such as aniline or heterocyclic amines such as melamine, contain methylol groups which are crosslinkable with the hydrolyzable metal compounds. Condensation products of other aldehydes are also effective.

The methylol groups of phenol- and amine-formaldehyde condensates may be partially etherified to increase solubility and to reduce crosslink density of the polymeric network formed on interaction with the hydrolyzable metal compound. The phenolic hydroxyl groups in a phenol-formaldehyde condensate may also be partially etherified.

Copolymers of hydroxyalkyl acrylates and methacrylates with other acrylic, vinyl or diene monomers, have crosslinkable hydroxyl groups whose concentration can be controlled by the monomer concentration. Other hydroxyl-containing copolymerizable monomers may be used, including N-methylolacrylamide, dihydroxypropyl methacrylate, etc. Suitable hydroxyl-containing polymers may also be prepared by post-reaction of suitable copolymers, e.g. methylolation of acrylamide copolymers with formaldehyde or other aldehydes, oxyalkylation of acrylic or methacrylic acid copolymers with alkylene oxide, hydrolysis of glycidyl methacrylate copolymers, reaction of glycidyl methacrylate copolymers with alkanolamines, etc.

In addition to the copolymerization of hydroxyl-containing monomers including allyl alcohol, alloxyethanol, 5-norbornene-2-methanol and the like, a route to hydroxyl-containing polymers includes the use of hydroxyl-containing catalysts or catalysts convertible to hydroxyl groups. Thus, hydroxyl-containing polybutadiene and other diene polymers and copolymers may be prepared by radical copolymerization or homopolymerization using hydrogen peroxide or $\beta$-hydroxyethyl alkyl peroxides as radical catalyst. Anionic polymerization of a diene monomer with lithium metal, followed by reaction of the resultant polymer with ethylene oxide yields a polydiene with terminal hydroxyl groups.

The hydrolysis of poly(allyl acetate), poly(vinyl acetate) and copolymers of allyl acetate or vinyl acetate or other allyl or vinyl esters yields polymers with hydroxyl groups. Partial hydrolysis of these homopolymers or copolymers yields copolymers containing hydroxyl groups and residual unhydrolyzed functionality. The hydrolyzed polymers may be reacted with aldehydes such as formaldehyde, butyraldehyde and benzaldehyde to yield formals and acetals containing residual hydroxyl groups capable of undergoing crosslinking. Oxyalkylation of the hydrolyzed polymers yields crosslinkable hydroxyalkyl derivatives.

Cellulose, starch, dextran, chitin and similar polyhydric natural polymers are useful in the practice of the present invention. In order to increase the solubilities of these materials in solvents, where necessary, ether and ester derivatives may be used, e.g. methyl cellulose, hydroxypropyl cellulose, cellulose acetate, cellulose acetate butyrate, etc.

Hydroxyl groups may be appended to polyamides and other polymers containing amide linkages, including block polyester-polyamides or polyether-polyamides, etc., or random copolymers containing amide linkages, including natural polymers such as polypeptides, by treatment with formaldehyde. The resultant methylolated amide functionality is crosslinkable by the hydrolyzable metal compounds of this invention. The polyamides may be of the 6,6-nylon type, prepared by the condensation of a dibasic acid and a diamine, including dimer acids, or of the 6-nylon type, prepared by the ring-opening polymerization of a lactam or the condensation of an aminoalkanoic acid.

Since the hydrolyzable metal compounds of use in the present invention are polyfunctional, it is generally desirable that the reactive hydroxyl-containing polymer be of low molecular weight and/or have a low hydroxyl content to control crosslink density.

The preferred compositions of the present invention contain hydroxyl-containing polymers and hydrolyzable silanes and titanium compounds in weight ratios wherein the ratio of hydroxyl-containing polymer to the sum of silane and titanium compound is from 99.9/0.1 to 0/100 and the ratio of silane to titanium compound is from 0.1/99.9 to 99.9/0.1.

The use of hydrolyzable silanes as adhesion promoting agents is well known. The silane "coupling agents" act as bridges between polymers and fillers or reinforcing agents and permit increased filler loadings, higher reinforcement levels and improved processing and end-product properties in thermosetting resins, thermoplastic resins and elastomers (J. G. Marsden, Plastics Compounding, 1, No. 2, 32 (July/August 1978).

The use of organic titanates and titanium chelates to modify solid surfaces in order to improve adhesion is well known. The titanium compounds are generally applied to the solid surface of a metal, glass or polymer to form an amorphous film of titanium dioxide upon hydrolysis. The hydrolyzed primed surface functions as a polar surface for lamination to a polymeric film or metallic foil or bonding to a coating (U.S. Pat. Nos. 2,751,314, 2,768,909 and 2,838,418).

The organic titanates have been used as catalysts for the polymerization of many types of polysiloxanes. Their use permits more rapid cures at lower temperatures than could otherwise be obtained. In many of these reactions, the titanates serve as catalysts and also crosslink the polysiloxane structure (U.S. Pat. Nos. 2,732,320, 3,014,826, 3,647,846, 3,015,637 and 2,721,855). The disclosures of each of the hereinabove identified references are incorporated herein by reference.

The use of titanates and titanium chelates for the crosslinking of hydroxyl-containing polymers, particularly those used in paint vehicles and printing inks, is well known to those skilled in the art. The use of titanates permits more rapid cure at lower temperatures than could otherwise be obtained.

The toughness, heat resistance, solvent resistance and other properties of coatings based on alkyd resins (M. A. Lerman, Journal of Coatings Technology, 48, 37 (December 1976), polyester resins (U.S. Pat. Nos. 3,074,818 and 3,382,203), bisphenol A-based epoxy resins (U.S. Pat. No. 2,742,448) and other hydroxyl-containing resins are improved on crosslinking with hydrolyzable titanates and titanium chelates.

The drying time and temperature of printing inks containing nitrocellulose (U.S. Pat. No. 2,732,799), rosin esters of pentaerythritol and glycerol (U.S. Pat. No. 3,682,688) and other polyhydroxy compounds are reduced by the use of organic titanates and chelates.

Cellulose (P. Legally and H. Legally, TAPPI, 39, No. 11 (1956) and cellulose acetate fibers (U.S. Pat. No. 3,033,698) are crosslinked in the presence of titanium chelates. The disclosures of each of the hereinabove identified references are incorporated herein by reference.

It is surprising, in view of the disclosures of the prior art, that a microbiocide can be incorporated into a reactive composition containing a hydrolyzable titanium compound and a hydrolyzable silane and that on application to a suitable surface and reaction with moisture at ambient temperature, the hydrolyzable compounds undergo crosslinking per se, or crosslink a hydroxyl-containing polymer when the latter is present, to generate an adherent polymeric network or matrix capable of controlling the release of the microbiocide incorporated therein.

The microbiocides which may be used in the practice of the present invention are well known for their efficacy as disinfectants and preservatives. They include chlorine compounds, iodine compounds, phenols and bisphenols, salicylanilides and carbanilides, alcohols, quaternary ammonium compounds, anionic and amphoteric surfactants, mercurials, silver compounds and formaldehyde donors and the like.

Representative chlorine compounds include Chloroazodin (N,N'-dichloroazodicarbonamidine), Chloramine T (sodium p-toluenesulfonchloramide), Dichloramine T (p-toluenesulfondichloramide), Chloramine B (sodium benzenesulfonchloramide), succinchlorimide, Halazone (p-sulfondichloramidobenzoic acid), Halane (1,3-dichloro-5,5-dimethylhydantoin), dichloroisocyanuric acid, trichloroisocyanuric acid, sodium and potassium dichloroisocyanurate, trichloromelamine as well as other chlorinated derivatives of urea, diamines, amides, imides and sulfonamides.

Representative iodine compounds include iodophors, i.e. combinations of iodine and a carrier, and organic iodine compounds. Typical iodophors include polyvinylpyrrolidone-iodine, polyethoxypolypropoxypolyethoxyethanol-iodine, nonylphenoxypolyoxyethanol-iodine, undecoylium chloride-iodine and the like. Useful iodine compounds include iodoform, thymol iodide, bismuth formic iodide, bismuth oxyiodopyrogallate, ethyl diiodosalicylate, and iodonium compounds.

Representative phenolic comounds include phenol, cresols, xylenols, alkyl phenols, bis(hydroxyphenyl)alkanes, coal tar and tar oil, alkyl derivatives of chloro- and bromophenol such as o-butyl-p-chlorophenol as well as polyalkyl and aromatic derivatives of mono- and polyhalophenols, thymol, carvacrol, p-chloro-o-benzylphenol, dihydric phenols and derivatives such as 4-n-hexylresorcinol, halo-4-benzylresorcinol, hydroxycarboxylic acids and esters such as propyl and butyl p-hydroxybenzoates, nitrophenols, 8-hydroxyquinoline, bisphenols such as Dichlorophene[2,2'-methylenebis(4-chlorophenol)], Tetrachlorophene[2,2'-methylenebis(4,6-dichlorophenol)], Hexachlorophene[2,2'-methylenebis(3,4,6-trichlorophenol)], Bithionol[2,2'-thiobis(4,6-dichlorophenol)] and the like.

Representative salicylanilides include unsubstituted salicylanilide, dibromosalicylanilide, Tribromosalan, Fluorosalan (trifluoromethylsalicylanilide) and the like. Effective carbanilides include Triclocarban (3,4,4'-trichlorocarbanilide), Cloflucarban (3-trifluoromethyl-4,4'-dichlorocarbanilide), etc.

Representative quaternary ammonium compounds include monoalkyltrimethyl ammonium salts such as CTAB (cetyltrimethylammonium bromide), Arquad 16 (alkyltrimethyl ammonium chloride) and Gloquat C (alkylaryltrimethyl ammonium chloride), monoalkyldimethylbenzyl ammonium salts such as BTC 824, Hyamine 3500, Cyncal Type 14, Catigene (alkyldimethylbenzyl ammonium chlorides) and Riseptin (dodecyldimethyl-3,4-dichlorobenzyl ammonium chloride), dialkyldimethyl ammonium salts such as Deciquam 222 (didecyldimethyl ammonium halide) and BTC 812 (octyldodecyldimethyl ammonium chloride), heteroaromatic ammonium salts such as CPC and Ceepryn (cetylpyridinium halide) and Isothan Q (alkylisoquinolinium bromide), polysubstituted quaternary ammonium salts such as Loroquat QA 100 and Onyxide 3300 (alkyldimethylbenzyl ammonium saccharinate), bis-quaternary ammonium salts such as Dequadin [1,10-bis(2-methyl-4-aminoquinolinium chloride)decane] and polymeric quaternary ammonium salts such as WSCP [poly-(oxyethylene)dimethyliminoethylenedimethyliminoethylene dichloride].

Representative mercurials include calomel, acetomeroctol [2-(acetoxymercuri)-4-(1,1',3,3'-tetramethylbutyl)phenol], mercurochrome (disodium 2,7-dibromo-4-hydroxymercurifluorescein), phenylmercuric borate, merthiolate (sodium ethylmercurithiosalicylate) and o-(chloromercuri)phenol.

These and other microbiocides have been described in "Disinfection, Sterilization and Preservation", edited by S. S. Block, 2nd Edition, Lea & Febiger, Philaldelphia, Pa, 1977, the disclosures of which are incorporated herein by reference.

The microbiocide is included in the composition in an amount sufficient to exert a microbiocidal action on the immediate environment surrounding the substrate. The amount of microbiocide will be dependent upon several factors such as the composition and thickness of the crosslinked polymeric matrix, the nature of the microbiocide, i.e. liquid or solid, the presence of active hydrogen functionality, the duration of microbiocidal action desired, etc. The optimum amount of microbiocide to be included may readily be determined by those skilled in the art. Generally, from about 1 part by weight of microbiocide to 0.5 to 1,000,000 parts of reactive components, i.e. hydrolyzable compounds and hydroxyl-containing polymer, when the latter is present, is satisfactory.

The compositions of this invention may include volatile diluents such as aliphatic or aromatic hydrocarbons, e.g. Stoddard Solvent, mineral spirits, B&P naphtha, cyclohexane, petroleum ether, toluene, xylene, etc., halogenated hydrocarbons such as perchloroethylene and fluorocarbons or volatile fluid polysiloxanes such as dimethylpolysiloxane fluids. The compositions may be prepared by merely admixing the various components. Before mixing, the components may be dispersed or dissolved in a diluent, such as previously described or a volatile alcohol. The compositions may also be prepared in aqueous media when slowly hydrolyzing and/or stable components are present.

The compositions of this invention may be applied to a large number of substrates. The substrate should preferably be one which contains active hydrogen atoms which provide sites for interaction with the crosslinkable compounds. Thus, surfaces on land or marine structures including ships, docks and buildings such as homes, institutions, hospitals, restaurants, farm buildings, office buildings and the like, and walls, floors, cellings, doors, windows and furnishings in rooms in such buildings including offices, kitchens, bedrooms, bathrooms, closets, changing rooms, waiting rooms, operating rooms, supply rooms, swimming pools, etc., may be treated with the compositions of this invention. In addition to wood, plaster board, metal, brick, wall paper, glass, ceramic tile and other surfaces and surfacing materials may serve as substrates. Furnishings include curtains, rugs, wall coverings, bed coverings, blankets, bed sheets, as well as clothing made of woven or nonwoven natural or synthetic fibers may also serve as substrates. Various containers such as bags, cardboard and wooden boxes, metal cans, glass containers and the like may also serve as substrates in accordance with the practice of this invention. Human and animal skin and other surfaces are also suitable substrates.

The compositions of this invention may be applied to the substrate by brushing, spraying, dipping, wiping or any other known method for applying a fluid composition to a solid substrate. It may be applied in the form of an aerosol mist or fog, propelled by conventional pressurized volatile halohydrocarbon, hydrocarbon or compressed gas propellants, an air propelled mist blower or other suitable means.

Although this invention should not be limited thereby, it is believed that upon application of the compositions of this invention to a suitable substrate in an ambient atmosphere, evaporation of the volatile diluent, if any is present, and exposure to atmospheric moisture results in the hydrolysis of both the hydrolyzable titanium compound and the hydrolyzable silane, followed by condensation of the $Ti(OH)_x$ and $Si(OH)_y$ groups generated thereby with each other and with the hydroxyl groups of the hydroxyl-containing polymer, if the latter is present, to form a crosslinked polymer-polymetalloxane and/or polymetalloxane matrix containing entrapped or occluded microbiocide. Simultaneously, the $Ti(OH)_x$ and/or $Si(OH)_y$ groups promote the adhesion of the crosslinked matrix and the microbiocide therein to the substrate. Adhesion to the substrate is due at least in part to the fact that the crosslinked matrix or network is coupled to the substrate by reaction through active hydrogen atoms on the substrate. In this manner, the microbiocide is held on the substrate to such an extent that it cannot be physically brushed off, blown off, wiped off or washed off. Further, as a result of its entrapped condition the rapid evaporation, sublimation or extraction of the microbiocide is retarded. However, due to the permeability of the matrix, said evaporation or sublimation is not completely inhibited, resulting in controlled release of the microbiocide.

When water is present in the compositions of this invention, said water is generally added shortly before application of the composition to a suitable substrate, and hydrolysis of the titanium compound and silane may begin before or during application to said substrate. However, hydrolysis continues after said application and is followed by condensation of the $Ti(OH)_x$ and $Si(OH)_y$ groups generated thereby with each other, the hydroxyl groups on the hydroxyl-containing polymer when the latter is present, and the active hydrogen actoms on the substrate.

When a water stable titanium compound, e.g., an organic titanium chelate such as the lactic acid chelate or the triethanolamine chelate, is present, the aqueous composition may be prepared long before application to the substrate. However, an acid or acid-generating compound is added to the aqueous composition containing the triethanolamine chelate or a base or base-generating compound is added to the composition containing the lactic acid chelate, shortly before application to the substrate. The resultant change in the pH promotes hydrolysis of the titanium chelate, which may begin before or during application to the substrate. However, hydrolysis continues after said application and is followed by condensation of the hydroxyl groups generated thereby with the hydroxyl groups on the polymer and the active hydrogen atoms on the substrate.

The rate of release of the microbiocide may be controlled by adjusting the extent of crosslinking, e.g. by adjusting the ratio of polymer and hydrolyzable silane and titanium compounds, the thickness of the polymer coating, i.e. by modifying the concentration of reactive components in the solution thereof, or by adding a non-volatile, non-reactive extender for the crosslinked polymer. The latter may have the same structure as the hydroxyl-containing polymer except for the absence of reactive functionality or have a solubility parameter in the same range as that of the polymer. The extender functions essentially as a plasticizer and appropriate plasticizers or extenders for a particular hydroxyl-containing polymer are well known to those skilled in the art.

A typical non-volatile, non-reactive extender for the crosslinked polysiloxane may be a compatible non-siloxane compound, e.g. a hydrocarbon oil, or may be an alkyl or an alkylarylpolysiloxane fluid having a viscosity ranging from 5 to 100,000 centistokes at 25° C.

Typical plasticizers or extenders for hydroxyl-containing polyalkylene oxides, e.g. polyethylene oxide, polyoxyalkylated polyols, polytetrahydrofuran or polytetramethylene glycol, as well as polyesters including polycaprolactone polyols, contain polyether linkages and are free of hydroxyl groups, e.g. dipropylene glycol dibenzoate, polyethylene glycol distearate, and the like. Acrylic copolymers containing hydroxyalkyl acrylates or methacrylates may be extended by simple esters such as dioctyl phthalate or azelates or trimellitates or polymeric esters such as poly(ethylene-co-propylene adipate) which has been end-capped by esterification so that it is free of hydroxyl groups, or acrylic copolymers such as poly(butyl acrylate) or poly(ethylhexyl acrylate), preferably of low molecular weight. Similar plasticizers or extenders are useful with vinyl acetate homopolymer or copolymers which have been fully or partially hydrolyzed, as well as cellulose ethers or esters, polyvinyl formals or epoxy resins. Sucrose acetate isobutyrate is an effective extender for polyvinyl formal and polyvinyl butyral. Hydrocarbon polymers such as hydroxyl-containing polybutadiene or butadiene copolymers may be extended with polybutadienes, liquid polybutylenes or polypropenes, poly-α-methylstyrenes, terpene resins and other hydrocarbon resins and oils. This partial listing of typical extenders is representative of the low molecular compounds and polymers which are compatible with the hydroxyl-containing polymers of interest in the practice of this invention.

In addition to or in lieu of the solvents which function to reduce the viscosity of the compositions of this invention, as well as reduce the thickness of the polymer coating, volatile alcohols such as ethanol, isopropanol, butanol and the like may be included in the composition to prevent premature hydrolysis of the hydrolyzable crosslinking agent with resultant gelation and precipitation.

Other additives which may be incorporated into the compositions of this invention include stabilizers against environmental degradation, such as antioxidants and ultraviolet stabilizers, odor masking compounds and perfumes, dyes, pigments, fillers, etc.

Since the adherent controlled release microbiocidal compositions of the present invention contain microbiocides having known activity against either a wide spectrum of microorganisms, including Gram-negative and Gram-positive bacteria and viruses, or selective toxicity towards a specific microorganism, they may be used to provide an improvement over existing technology in the same areas where a given microbiocide has previously been used.

Thus, phenolic compounds may be used as microbiocides against *Salmonella typhosa, Staphylococcus aureus, Escherichia coli* and *Mycobacterium tuberculosis.* Bisohenols are effective against *S. aureus, E. coli* and *Bacillus subtilis.* Salicylanilides and carbanilides are effective against *Aerobacter aerogenes, S. aureus* and *B. subtilis.* Quaternary ammonium compounds are effective against E. coli, S. aureus and S. typhosa, as well as influenza, vaccinia, Coxsackie, herpes simplex and polio viruses. These and other interactions are described in the previously cited "Disinfection, Sterilization and Preservation, edited by S. S. Block, the disclosures of which are incorporated herein by reference.

The advantages of the compositions of the present invention over those of the prior art include the opportunity to improve thereupon, i.e. the opportunity to use known toxic agents against known microorganisms while decreasing the frequency of application and, generally, the concentration of microbiocide per application. Obviously, the technology disclosed herein, will be applicable to the controlled release of new microbiocides when the efficacy of the latter have been demonstrated.

What is claimed is:

1. A composition capable of undergoing hydrolysis under ambient conditions to form a polymeric network capable of controlling the release of a microbiocide, consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) a hydrolyzable titanium compound or a partial hydrolyzate thereof, said titanium compound being selected from the group consisting of (1) tetraesters, tetraanhydrides and tetraamides, and (2) chelates of glycols, hydroxy acids, dicarboxylic acids, diketones, ketoesters and alkanolamines, and (c) a microbiocide.

2. A composition capable of undergoing hydrolysis under ambient conditions to form a polymeric network capable of controlling the release of a microbiocide, consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) a hydrolyzable titanium compound or a partial hydrolyzate thereof, said titanium compound being selected from the group consisting of (1) tetraesters, tetraanhydrides and tetraamides, and (2) chelates of glycols, hydroxy acids, dicarboxylic acids, diketones, ketoesters and alkanolamines, (c) a hydroxyl-containing polymer selected from the group consisting of (1) an organopolysiloxane containing hydroxyl groups or functional groups which are hydrolyzable to hydroxyl groups, and (2) a carbinol-containing polymer, and (d) a microbiocide.

3. The composition of claim 1 wherein the hydrocarbon substituted hydrolyzable silane has the formula $R_nSiX_{4-n}$ where R is a monovalent hydrocarbon radical, X is a hydrolyzable group selected from the group consisting of halogen, alkoxy, acyloxy and hydrogen, and n is an integer from 0 to 2.

4. The composition of claim 1 wherein the organopolysiloxane containing hydrolyzable silane groups has the formula $P-(SiX_n)_m$ where P is an organopolysiloxane, X is a hydrolyzable group selected from the group consisting of halogen, alkoxy, acyloxy and hydrogen, n is an integer from 2 to 3, and m is an integer from 1 to 20.

5. The composition of claim 4 wherein the organopolysiloxane contains the structural unit:

wherein R''' and R'''' are oxygen or non-hydrolyzable hydrocarbon or heterocyclic radicals.

6. The composition of claim 5 wherein the non-hydrolyzable radicals are selected from the group consisting of acyclic or cyclic, saturated or unsaturated aliphatic radicals, aromatic radicals, aralkyl radicals and alkylaryl radicals.

7. The composition of claim 2 wherein the hydrocarbon substituted hydrolyzable silane has the formula $R_nSiX_{4-n}$ where R is a monovalent hydrocarbon radical, X is a hydrolyzable group selected from the group consisting of halogen, alkoxy, acyloxy and hydrogen, and n is an integer from 0 to 2.

8. The composition of claim 2 wherein the organopolysiloxane containing hydrolyzable silane groups has the formula $P-(SiX_n)_m$ where P is an organopolysiloxane, X is a hydrolyzable group selected from the group consisting of halogen, alkoxy, acyloxy and hydrogen, n is an integer from 2 to 3, and m is an integer from 1 to 20.

9. The composition of claim 8 wherein the organopolysiloxane contains the structural unit:

wherein R''' and R'''' are oxygen or non-hydrolyzable hydrocarbon or heterocyclic radicals.

10. The composition of claim 9 wherein the non-hydrolyzable radicals are selected from the group consisting of acyclic or cyclic, saturated or unsaturated aliphatic radicals, aromatic radicals, aralkyl radicals and alkylaryl radicals.

11. The composition of claim 2 wherein the organopolysiloxane contains the structural unit

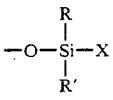

wherein X is a hydroxyl radical or a hydrolyzable radical and R and R' are oxygen or non-hydrolyzable hydrocarbon or heterocyclic radicals.

12. The composition of claim 11 wherein the hydrolyzable groups on the organopolysiloxane are selected from the group consisting of halogen, alkoxy, acyloxy and hydrogen.

13. The composition of claim 11 wherein the non-hydrolyzable hydrocarbon radicals are selected from the group consisting of branched, linear or cyclic aliphatic radicals, aromatic radicals, aralkyl radicals and alkylaryl radicals.

14. The composition of claim 1 wherein the weight ratio of (a) and (b) is within the range 0.1/99.9 to 99.9/0.1.

15. The composition of claim 2 wherein the weight ratio of (a+b)/c is within the range 0.1/99.9 to 99.9/0.1 and the weight ratio of (a) and (b) is within the range 0.1/99.9 to 99.9/0.1.

16. A composition capable of undergoing hydrolysis under ambient conditions to form a polymeric network capable of controlling the release of a microbiocide, consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) a hydrolyzable titanium compound or a partial hydrolyzate thereof, said titanium compound being selected from the group consisting of (1) tetraesters, tetraanhydrides and tetraamides, and (2) chelates of glycols, hydroxy acids, dicarboxylic acids, diketones, ketoesters and alkanolamines, (c) a hydroxyl-containing polymer selected from the group consisting of (1) an organopolysiloxane containing hydroxyl groups or functional groups which are hydrolyzable to hydroxyl groups, and (2) a carbinol-containing polymer, (d) a non-volatile, non-reactive extender, and (e) a microbiocide, wherein the weight ratio of (a+b)/c is within the range 0.1/99.9 to 100/0 and the weight ratio of (a) and (b) is within the range 0.1/99.9 to 99.9/0.1.

17. A composition capable of undergoing hydrolysis under ambient conditions to form a polymeric network capable of controlling the release of a microbiocide, consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) a hydrolyzable titanium compound or a partial hydrolyzate thereof, said titanium compound being selected from the group consisting of (1) tetraesters, tetraanhydrides and tetraamides, and (2) chelates of glycols, hydroxy acids, dicarboxylic acids, diketones, ketoesters and alkanolamines, (c) a hydroxyl-containing polymer selected from the group consisting of (1) an organopolysiloxane containing hydroxyl groups or functional groups which are hydrolyzable to hydroxyl groups, and (2) a carbinol-containing polymer, (d) a volatile diluent, and (e) a microbiocide, wherein the weight ratio of (a+b)/c is within the range 0.1/99.9 to 100/0 and the weight ratio of (a) and (b) is within the range 0.1/99.9 to 99.9/0.1.

18. A composition capable of undergoing hydrolysis under ambient conditions to form a polymeric network capable of controlling the release of a microbiocide, consisting essentially of (a) a hydrolyzable silane selected from the group consisting of (1) a hydrocarbon substituted hydrolyzable silane, and (2) an organopolysiloxane containing hydrolyzable silane groups, or a partial hydrolyzate thereof, (b) a hydrolyzable titanium compound or a partial hydrolyzate thereof, said titanium compound being selected from the group consisting of (1) tetraesters, tetraanhydrides and tetraamides, and (2) chelates of glycols, hydroxy acids, dicarboxylic acids, diketones, ketoesters and alkanolamines, (c) a hydroxyl-containing polymer selected from the group consisting of (1) an organopolysiloxane containing hydroxyl groups or functional groups which are hydrolyzable to hydroxyl groups, and (2) a carbinol-containing polymer, (d) a non-volatile, non-reactive extender, (e) a volatile diluent, and (f) a microbiocide, wherein the weight ratio of (a+b)/c is within the range 0.1/99.9 to 100/0 and the weight ratio of (a) and (b) is within the range 0.1/99.9 to 99.9/0.1.

19. A process for providing a substrate containing active hydrogen atoms with an adherent controlled release microbiocide which comprises applying the composition of claim 1 to said substrate and exposing the coated substrate to atmospheric moisture.

20. A process for providing a substrate containing active hydrogen atoms with an adherent controlled release microbiocide which comprises applying the composition of claim 2 to said substrate and exposing the coated substrate to atmospheric moisture.

21. A process for providing a substrate containing active hydrogen atoms with an adherent controlled release microbiocide which comprises applying the composition of claim 3 to said substrate and exposing the coated substrate to atmospheric moisture.

22. A process for providing a substrate containing active hydrogen atoms with an adherent controlled release microbiocide which comprises applying the composition of claim 4 to said substrate and exposing the coated substrate to atmospheric moisture.

23. A process for providing a substrate containing active hydrogen atoms with an adherent controlled release microbiocide which comprises applying the composition of claim 5 to said substrate and exposing the coated substrate to atmospheric moisture.

24. A process for providing a substrate containing active hydrogen atoms with an adherent controlled release microbiocide which comprises applying the composition of claim 6 to said substrate and exposing the coated substrate to atmospheric moisture.

25. A process for providing a substrate containing active hydrogen atoms with an adherent controlled release microbiocide which comprises applying the composition of claim 7 to said substrate and exposing the coated substrate to atmospheric moisture.

26. A process for providing a substrate containing active hydrogen atoms with an adherent controlled release microbiocide which comprises applying the composition of claim 8 to said substrate and exposing the coated substrate to atmospheric moisture.

27. A process for providing a substrate containing active hydrogen atoms with an adherent controlled release microbiocide which comprises applying the composition of claim 9 to said substrate and exposing the coated substrate to atmospheric moisture.

28. A process for providing a substrate containing active hydrogen atoms with an adherent controlled release microbiocide which comprises applying the composition of claim 10 to said substrate and exposing the coated substrate to atmospheric moisture.

29. A process for providing a substrate containing active hydrogen atoms with an adherent controlled release microbiocide which comprises applying the composition of claim 11 to said substrate and exposing the coated substrate to atmospheric moisture.

30. A process for providing a substrate containing active hydrogen atoms with an adherent controlled release microbiocide which comprises applying the composition of claim 12 to said substrate and exposing the coated substrate to atmospheric moisture.

31. A process for providing a substrate containing active hydrogen atoms with an adherent controlled release microbiocide which comprises applying the composition of claim 13 to said substrate and exposing the coated substrate to atmospheric moisture.

32. A process for providing a substrate containing active hydrogen atoms with an adherent controlled release microbiocide which comprises applying the composition of claim 14 to said substrate and exposing the coated substrate to atmospheric moisture.

33. A process for providing a substrate containing active hydrogen atoms with an adherent controlled release microbiocide which comprises applying the composition of claim 15 to said substrate and exposing the coated substrate to atmospheric moisture.

34. A process for providing a substrate containing active hydrogen atoms with an adherent controlled release microbiocide which comprises applying the composition of claim 16 to said substrate and exposing the coated substrate to atmospheric moisture.

35. A process for providing a substrate containing active hydrogen atoms with an adherent controlled release microbiocide which comprises applying the composition of claim 17 to said substrate and exposing the coated substrate to atmospheric moisture.

36. A process for providing a substrate containing active hydrogen atoms with an adherent controlled release microbiocide which comprises applying the composition of claim 18 to said substrate and exposing the coated substrate to atmospheric moisture.

* * * * *